United States Patent [19]
Stoughton

[11] 3,932,653
[45] Jan. 13, 1976

[54] COMPOSITION AND METHOD FOR TOPICAL ADMINISTRATION OF GRISEOFULVIN

[75] Inventor: Richard B. Stoughton, Rancho Santa Fe, Calif.

[73] Assignee: Nelson Research & Development Co., Irvine, Calif.

[22] Filed: Dec. 19, 1974

[21] Appl. No.: 534,227

[52] U.S. Cl. .................................... 424/285
[51] Int. Cl.[2] .................................... A61K 31/34
[58] Field of Search .................................... 424/271, 285

[56] References Cited

UNITED STATES PATENTS 3,773,959 11/1973 Nardo Zaias .................... 424/285

OTHER PUBLICATIONS

Chem. Abst. Vol. 73–102 083d, (1970).

*Primary Examiner*—Stanley J. Friedman
*Attorney, Agent, or Firm*—Martin A. Voet

[57] ABSTRACT

There is disclosed a method for topically administering griseofulvin to a human or animal in a manner such that a high degree of epidermal, especially stratum corneum, retention of griseofulvin is attained by contacting the skin of a human or animal with an effective amount of a therapeutic composition containing griseofulvin and 2-pyrrolidone or an N-lower alkyl-2-pyrrolidone.

6 Claims, No Drawings

COMPOSITION AND METHOD FOR TOPICAL ADMINISTRATION OF GRISEOFULVIN

BACKGROUND OF THE INVENTION

1. Field of the Invention

The invention relates generally to compositions and a method for topically administering griseofulvin to humans and animals. More particularly, the present invention relates to compositions and a method whereby griseofulvin is effectively administered topically to humans and animals and is retained by the epidermis and especially the stratum corneum in therapeutically effective amounts.

2. Background of the Prior Art

Griseofulvin is known as the treatment of choice for fungus infections of the skin and nails. Heretofore, the manner of delivery of griseofulvin has been oral. However, it has long been known that oral treatment is not perferred because of side effects resulting from saturation of the entire body with griseofulvin and the fact that only the outer layers of affected skin need to be treated. Therefore, because fungal infections are generally infections of the skin and nails, it would be advantageous to utilize griseofulvin topically. However, despite a long-felt need for a topical griseofulvin, griseofulvin has been used orally to treat topical fungus conditions because there was not heretofore known any formulation which could be safely delivered topically which would cause sufficient retention of griseofulvin in the skin to be useful therapeutically.

Vehicles such as USP cold cream, ethanol and various ointments, oils, solvents, and emulsions have been used to apply various chemically active ingredients locally. However, none of these are useful to cause continuous presence of therapeutically effective amounts of griseofulvin to be retained in the epidermis and especially the stratum corneum layers of the skin.

SUMMARY OF THE INVENTION

It has now unexpectedly been discovered that griseofulvin may be effectively administered topically through the use of compositions herein described.

The invention described herein generally relates to a method for topically administering griseofulvin to humans or animals and for retaining a therapeutically effective amount of griseofulvin in the epidermis. The invention also relates to compositions for use in the method.

The method specifically involves contacting human or animal skin or nails with an effective amount of a composition comprising griseofulvin together with 2-pyrrolidone or with an N-lower alkyl-2-pyrrolidone.

It has been found in experiments, both in vitro and in vivo, that through the use of the composition herein described, therapeutically effective amounts of griseofulvin are retained in the skin and/or nails.

DETAILED DESCRIPTION OF THE INVENTION

The amount of griseofulvin to be used in the present composition is that amount of griseofulvin which is effective therapeutically in the threatment of fungus diseases of the type in which griseofulvin is known to be useful, that is, an amount sufficient to temporarily alleviate the signs and symptoms of fungus diseases which are known to be treatable with griseofulvin. Typical therapeutic amounts are somewhat dependent on the particular fungus and its location, but these amounts generally range from about 0.1 to about 10% and preferably about 0.5 to about 5% by weight.

Griseofulvin may be dissolved in a vehicle of this invention and topically applied to affected areas of the skin in any convenient form, e.g. cream, lotion, spray, solution, etc.

2-Pyrrolidone and N-lower alkyl-2-pyrrolidones are available commercially and are made by a number of methods known to those of skill in the art as exemplified by U.S. Pat. Nos. 2,555,353 and 2,267,757. N-lower alkyl-2-pyrrolidones include the straight and branched chain lower alkyl groups having 1–4 carbon atoms. N-methyl-2-pyrrolidone is preferred.

The amount of 2-pyrrolidone or N-lower alkyl-2-pyrrolidone which may be used in the present invention ranges from about 5 to about 99.9 percent and preferably 10–50 percent by weight of the composition.

An effective amount of the composition, as the term is used herein, refers to that amount of composition which is effective thereapeutically in the treatment of fungus diseases. The composition is generally applied about 1–3 times daily in conventional amounts, that is, amounts sufficient to cover the affected areas. The treatment is continued until or sometime after all of the manifestations of the fungus infections have disappeared.

Ingredients which may be used in the formulations include conventional formulating ingredients, such as, for example, Freons, ethyl alcohol, isopropyl alcohol, acetone, fragrances, gel-producing materials, mineral oil, vegetable oils, PVP, water, stearyl alcohol, steric acid, spermaceti, sorbitan monooleate, Polysorbate 80, Tween 60, sorbital solutions, methylcellulose, etc.

The griseofulvin so applied is carried into and through the stratum corneum, and is retained in the epidermis and stratum corneum in the therapeutically effective amounts and thereby successfully treats fungus-caused skin problems. Griseofulvin, thus applied, as will be demonstrated hereinafter, is retained by the epidermis in far higher concentrations than was heretofore known and resists being removed by washing for substantial time periods whereby a successful therapeutic method of treatment is effected.

Following are specific examples which demonstrate the effectiveness of various forms of this invention.

EXAMPLE 1

EXAMPLE 1 indicates the radius of inhibition of griseofulvin when applied in the compositions of this invention as compared with when it is applied in conventional vehicles. The radius of inhibition indicates the radius of a spot on a culture in which complete inhibition of the growth of the indicated organisms is obtained when a piece of skin treated with the griseofulvin is placed on the culture. The radius of inhibition indicates the amount of material diffusing out of the skin and into the surrounding culture, and is directly proportional to the amount of griseofulvin retained in the skin following treatment. *T. mentagrophytes* is inhibited when treated with the indicated formulations. The data obtained are set forth in Table I.

TABLE I

| Radius of Inhibition of Griseofulvin | Human Skin | Hairless Mouse Skin |
|---|---|---|
| 1% Griseofulvin in | | |
| 1) N-methyl-2-pyrrolidone | 6 mm | 9 mm |
| 2) N-methyl-2-pyrrolidone 50% <br> Acetone 50% | 6 | 8 |

TABLE I-continued

| | Radius of Inhibition of Griseofulvin | |
|---|---|---|
| | Human Skin | Hairless Mouse Skin |
| 3) USP cold cream | 0 | 0 |
| 4) Ethyl alcohol | 0 | 0 |

EXAMPLE 2

Tests were made to determine whether the compositions of this invention caused therapeutically effective amounts of griseofulvin to be retained in human stratum corneum. A number of tests were run wherein 1% griseofulvin in the indicated vehicle was applied to skin areas on the upper arms of human subjects for 15 minutes and then washed with a standard soap and water solution and then rinsed in tap water. Samples of the stratum corneum were taken before the treatment and at the various hours indicated in Table II to measure the growth of *T. mentagrophytes* on those specimens. The growth of *T. mentagrophytes* was scored on a 0–3 basis with 0 being equivalent to no growth. Table II indicates the accumulated totals for six subjects having two samples each.

TABLE II

| | Stratum Corneum Retention of Griseofulvin | | | |
|---|---|---|---|---|
| | | Hours | | |
| 1% Griseofulvin in | 0 | 8 | 24 | 48 |
| N-methyl-2-pyrrolidone | 23 | 6 | 7 | 9 |
| USP cold cream | 25 | 23 | 27 | 25 |
| 95% ethanol | 22 | 21 | 23 | 22 |
| Acetone | 24 | 23 | 23 | 24 |
| Ointment base | 26 | 23 | 27 | 22 |

It is clear from TABLE II that griseofulvin applied in the form of conventional topical compositions is not retained by the epidermis, while griseofulvin applied in the form of the composition of this invention is retained by the skin in therapeutically effective amounts.

EXAMPLE 3

The retention of griseofulvin was also measured by applying compositions containing radioactive griseofulvin in vitro to specimens of human leg skin. Specimens were treated so that areas 3 cm$^2$ in diameter were covered with 0.01 cc of the indicated compositions; and after 15 minutes the specimens were washed with soap and water in a standard manner, after which the radioactivity was detected by a gas-flow skin counter which measures C$^{14}$ in the stratum corneum of the epidermis. After washing, the amount of radioactive carbon remaining was measured. The data collected are presented in TABLE III.

TABLE III

| | Percent Retention of Griseofulvin in Stratum Corneum after Washing |
|---|---|
| 0.1% C$^{14}$ Griseofulvin | Post-washing |
| in N-methyl-2-pyrrolidone | 12.2% |
| in ethyl alcohol | 0.0% |
| in USP cold cream | 0.8% |

This example indicates that none or only insubstantial amounts of griseofulvin are retained by the epidermis using conventional topical composition, while substantial quantities of griseofulvin are retained by the skin using the composition of this invention.

EXAMPLE 4

EXAMPLE 3 was repeated, except the study used 1% griseofulvin rather than 0.1% and the study was carried out for 72 hours. Table IV below tabulates the results of the study.

TABLE IV

| | Percent Retention of 1% Griseofulvin in Stratum Corneum after Washing | | | |
|---|---|---|---|---|
| 1% C$^{14}$ Griseofulvin | Immediate | 8 hours | 24 hours | 72 hours |
| in N-methyl-2-pyrrolidone | 18.5% | 14.2% | 7.1% | 4.1% |
| USP cold cream | 1.3% | 0.2% | 0.0% | 0.0% |
| Ethyl alcohol | 0.9% | 0.3% | 0.0% | 0.0% |

EXAMPLE 5

The following solution formulations were prepared.

| | SOLUTIONS | | |
|---|---|---|---|
| | A | B | C |
| Griseofulvin | 1% | 1% | 1% |
| N-methyl-2-pyrrolidone | 10% | 46.6% | 90% |
| Isopropyl myristate | 5% | 5% | 5% |
| Fragrance | 0.1% | 0.1% | 0.1% |
| Adjuvant solvent q.s.ad | ethanol | isopropyl alcohol | acetone |

Formulation B was tested on human subjects with fungus infections on the feet or hands. The subjects indicated that the formulation stopped the itching and cleared the fungus with daily application over a period of 2–4 weeks.

EXAMPLE 6

An aerosol form of formulation B of EXAMPLE 5 is prepared by preparing the following mixture:

| formulation B | 25% |
|---|---|
| Freon$^1$ | 75% |

$^1$Freon is 75/25 Freon 114/12.

EXAMPLE 7

The following gel formulations were prepared:

| | Gel | |
|---|---|---|
| | A | B |
| Griseofulvin | 1% | 1% |
| N-methyl-2-pyrrolidone | 96% | 20% |
| Carbopol 934 | 1% | — |
| Carbopol 940 | — | 0.75% |
| Ethanol | — | 50% |
| Ethoxyl 16R | — | 2% |
| Diethanolamine | — | 0.5% |
| di-2(ethylhexyl)amine | 2% | — |
| water q.s.ad | | |

EXAMPLE 8

The following cream formulations were prepared:

| | Creams | | | |
|---|---|---|---|---|
| | A | B | C | D |
| Griseofulvin | 1% | 1% | 1% | 1% |
| N-methyl-2-pyrrolidone | 25% | 20% | 34% | 42% |
| Stearyl alcohol | 12% | — | — | 10% |
| Stearic acid | — | 19% | 18% | 6% |

-continued

| | Creams | | | |
|---|---|---|---|---|
| | A | B | C | D |
| Synthetic spermaceti | 7.5% | — | 2% | 4% |
| Sorbitan monooleate | 1.0% | — | — | — |
| Polysorbate 80 | 5.5% | — | — | — |
| Tween 60 | — | 3.5% | 3.5% | 3.5% |
| Arlacel 60 | — | 1.5% | 3.5% | 1.5% |
| Sorbitol solution | 5.5% | 19.4% | 14.0% | 10.5% |
| Mineral oil | — | 2.0% | — | — |
| Methocel 90 HG-100 | — | 0.2% | 0.2% | 0.2% |
| Fragrances | 0.2% | — | — | — |
| Sodium citrate | 0.5% | — | — | — |
| Water q.s.ad | | | | |

EXAMPLE 9

Examples 1-4 are repeated, except the following compounds are used instead of N-methyl-2-pyrrolidone: 2-pyrrolidone, N-ethyl-2-pyrrolidone, N-propyl-2-pyrrolidone and N-isobutyl-2-pyrrolidone. Comparable results are obtained.

I claim:

1. A composition useful in the topical treatment of fungal infections of the skin and nails comprising about 0.1 to about 10 percent by weight of griseofulvin together with about 5 to about 99.9 percent by weight of a compound selected from the group consisting of 2-pyrrolidone and an N-lower alkyl-2-pyrrolidone.

2. The composition of claim 1 wherein the N-lower alkyl substitutent has 1-4 carbon atoms.

3. A composition useful in the topical treatment of fungal infections of the skin and nails comprising about 0.1 to about 10 percent by weight of griseofulvin together with about 5 to about 99.9 percent by weight of N-methyl-2-pyrrolidone.

4. A method for effectively administering a therapeutic amount of griseofulvin topically to humans or animals comprising contacting human or animal skin or nails with an effective amount of a therapeutic composition containing about 0.1 to about 10 percent by weight of griseofulvin together with about 5 to about 99.9 percent by weight of a compound selected from the group consisting of 2-pyrrolidone and an N-lower alkyl-2-pyrrolidone.

5. The method of claim 4 wherein the N-lower alkyl substituent has 1-4 carbon atoms.

6. The method of claim 4 wherein the compound is N-methyl-2-pyrrolidone.

* * * * *